United States Patent
Fukutani

(10) Patent No.: US 9,572,531 B2
(45) Date of Patent: Feb. 21, 2017

(54) OBJECT INFORMATION ACQUIRING APPARATUS AND CONTROL METHOD THEREOF

(71) Applicant: CANON KABUSHIKI KAISHA, Tokyo (JP)

(72) Inventor: Kazuhiko Fukutani, Kyoto (JP)

(73) Assignee: CANON KABUSHIKI KAISHA, Tokyo (JP)

(*) Notice: Subject to any disclaimer, the term of this patent is extended or adjusted under 35 U.S.C. 154(b) by 63 days.

(21) Appl. No.: 14/203,787

(22) Filed: Mar. 11, 2014

(65) Prior Publication Data

US 2014/0286549 A1  Sep. 25, 2014

(30) Foreign Application Priority Data

Mar. 21, 2013 (JP) ................... 2013-057791

(51) Int. Cl.
*G06K 9/00* (2006.01)
*A61B 5/00* (2006.01)

(52) U.S. Cl.
CPC ............ *A61B 5/489* (2013.01); *A61B 5/0095* (2013.01)

(58) Field of Classification Search
None
See application file for complete search history.

(56) References Cited

U.S. PATENT DOCUMENTS

| | | | |
|---|---|---|---|
| 7,864,307 B2 | 1/2011 | Fukutani et al. ............... 356/73 |
| 2010/0049044 A1* | 2/2010 | Burcher ........................ 600/437 |
| 2010/0087733 A1 | 4/2010 | Nakajima et al. ............ 600/437 |
| 2013/0109947 A1* | 5/2013 | Wood ............................. 600/407 |
| 2014/0073907 A1* | 3/2014 | Kumar ................... A61B 10/00 600/414 |
| 2014/0235993 A1 | 8/2014 | Fukutani ....................... 600/407 |
| 2014/0360271 A1 | 12/2014 | Fukutani |
| 2015/0031990 A1* | 1/2015 | Boctor et al. ................. 600/424 |
| 2015/0051888 A1* | 2/2015 | Itu et al. .......................... 703/2 |
| 2015/0245771 A1* | 9/2015 | Wang .................. A61B 5/0095 600/411 |

OTHER PUBLICATIONS

Firouzi et al (NPL: "A Numerical model for the study of photoacoustic imaging of brain tumors", Standford Universirty, University College. p. 17, 2011).*
M. Xu et al., "Photoacoustic Imaging in Biomedicine", *Review of Scientific Instruments*, 77, 041101 (Apr. 17, 2006).
Y. Xu et al., "Reconstructions in Limited-View Thermoacoustic Tomography", *Medical Physics*, vol. 31, No. 4 (Mar. 11, 2004).
Treeby, et al., k-Wave: MATLAB toolbox for the simulation and reconstruction of photoacoustic wave fields, J Biomed. Opt., vol. 15, No. 2 (2010) 021314-1-12.

* cited by examiner

*Primary Examiner* — Oneal R Mistry
(74) *Attorney, Agent, or Firm* — Fitzpatrick, Cella, Harper & Scinto

(57) ABSTRACT

Provided is an object information acquiring apparatus having: a light source; a probe that converts an acoustic wave generated from an object, onto which light is irradiated from the light source, into a detection signal; and a signal processor that obtains characteristic information inside the object based on the detection signal, wherein the signal processor obtains the characteristic information using information regarding a characteristic structure of a measurement target inside the object.

15 Claims, 5 Drawing Sheets

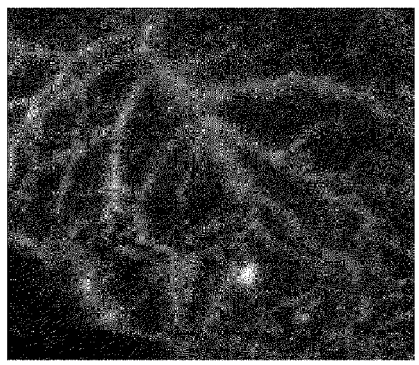 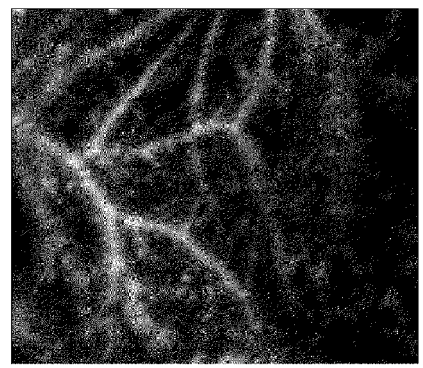
FIG. 4A                    FIG. 4B

OBJECT INFORMATION ACQUIRING APPARATUS AND CONTROL METHOD THEREOF

BACKGROUND OF THE INVENTION

Field of the Invention

The present invention relates to an object information acquiring apparatus and a control method thereof.

Description of the Related Art

Vigorous research on optical imaging apparatuses where light is irradiated onto an object, such as an organism, from a light source that is a laser or the like, and where information in the object acquired based on the entered light is imaged, is progressing in medical fields. One optical imaging technique is photoacoustic imaging (PAI). In photoacoustic imaging, pulsed light generated in a light source is irradiated onto an object. Thereby an acoustic wave (typically, an ultrasound wave) is generated from a tissue of the object (light absorber) which absorbed the energy of the pulsed light which propagated and diffused in the object. The object information is imaged based on a signal which is detected as an acoustic wave by a probe or the like and is outputted. In other words, the photoacoustic imaging is a technique to analyze a signal received by a probe, that is, an acoustic wave generated when a measurement target segment absorbs light energy and expands instantaneously, and to image a difference of absorptivity of the light energy between such a measurement segment as a tumor and other tissue. By this analysis processing, an optical characteristic distribution in the object, particularly an initial sound pressure distribution, a light energy absorption density distribution, an absorption coefficient distribution or the like can be obtained. These distributions can be used for measuring a specific substance in an object, such as oxygen saturation in blood. In recent years, pre-clinical research to image the blood vessel images of small animals using this photoacoustic imaging and clinical research to apply this theory to the diagnosis of breast cancer are actively promoted (see "Photoacoustic imaging in biomedicine", M. Xu, L. V. Wang, REVIEW OF SCIENTIFIC INSTRUMENT, 77, 041101, 2006).

Non Patent Literature 1: "Photoacoustic imaging in biomedicine", M. Xu, L. V. Wang, REVIEW OF SCIENTIFIC INSTRUMENT, 77, 041101, 2006

Non Patent Literature 2: "Reconstructions in limited-view thermoacoustic tomography", Y. Xu and L. V. Wang, Medical Physics, 31(4), 724, 2004

SUMMARY OF THE INVENTION

In an ideal photoacoustic imaging apparatus, an image is reconstructed by receiving an acoustic wave all around a closed surface surrounding an object. However if the acoustic wave measurement area is insufficient for an area to be imaged, the acoustic wave may be received only from a certain direction. This state is called a "limited view condition". Under such a condition, the shape of a light absorber, which is an acoustic wave generation source, cannot be perfectly reproduced by a general image reconstruction method, such as a back projection method. Furthermore, it is known that streak artifacts are generated in an area of which shape cannot be reproduced (see "Reconstructions in limited-view thermoacoustic tomography", Y. Xu and L. V. Wang, Medical Physics, 31(4), 724, 2004).

With the foregoing in view, it is an object of the present invention to provide a technique to decrease artifacts even under a limited view condition, and to improve the reproducibility of the shape of the acoustic wave generation source.

The present invention provides an object information acquiring apparatus, comprising:
a light source;
a probe configured to convert an acoustic wave generated from an object, onto which light is irradiated from the light source, into a detection signal; and
a signal processor configured to obtain characteristic information inside the object based on the detection signal, wherein
the signal processor obtains the characteristic information using information regarding a characteristic structure of a measurement target inside the object.

The present invention also provides a control method of an object information acquiring apparatus that includes a light source, a probe and a signal processor, the control method comprising:
a step in which the probe converts an acoustic wave generated from an object, onto which light is irradiated from the light source, into a detection signal;
a step in which the signal processor obtains characteristic information inside the object based on the detection signal; and
a step in which the signal processor obtains the characteristic information using information regarding a characteristic structure of a measurement target inside the object.

According to the present invention, a technique to decrease artifacts even under a limited view condition, and improve the reproducibility of the shape of the acoustic wave generation source can be provided.

Further features of the present invention will become apparent from the following description of exemplary embodiments with reference to the attached drawings.

BRIEF DESCRIPTION OF THE DRAWINGS

FIG. 4A and FIG. 4B are examples of a blood vessel image used for image reconstruction.

DESCRIPTION OF THE EMBODIMENTS

Preferred embodiments of the present invention will now be described with reference to the drawings. The dimensions, materials, shapes, relative arrangements or the like of the composing elements to be described hereinbelow should be changed appropriately depending on the configuration and the various conditions of the apparatus to which the invention is applied, and are not intended to limit the scope of the invention to the following description.

An object information acquiring apparatus of the present invention is an apparatus that utilizes the photoacoustic effect, where an acoustic wave, that is generated by irradiating the light (electromagnetic wave) onto an object and propagating in the object, is received, and object information, which is characteristic information on the object, is acquired as image data. The acquired object information is characteristic information to indicate the generation source distribution of an acoustic wave generated by light irradiation, the initial sound pressure distribution in the object, the light energy absorption density distribution and the absorption coefficient distribution derived from the initial sound pressure distribution, and the concentration distribution of a substance which constitutes a tissue, for example. The substance which constitutes a tissue is, for example, blood components indicated in the oxygen saturation distribution and in the oxyhemoglobin/deoxyhemoglobin concentration distribution, lipids, collagen or water.

The acoustic wave in the present invention is typically an ultrasound wave, including an elastic wave called sound wave and acoustic wave. An acoustic wave generated by the photoacoustic effect is called a "photoacoustic wave" or a "light-induced ultrasound wave". In the apparatus of the present invention, an acoustic wave generated and propagated or reflected and propagated in the object is received by an acoustic wave detector, such as a probe.

The object information acquiring apparatus of the present invention can be applied to a photoacoustic imaging apparatus that generates a display image by analyzing detection signals (received signals) of a photoacoustic wave. This photoacoustic imaging apparatus will be described hereinbelow. However the application targets of the present invention are not limited to a photoacoustic imaging apparatus. For example, the present invention can be applied to an apparatus that acquires characteristic information for forming an image and storing this information in a memory. The present invention can also be understood as a control method of an object information acquiring apparatus, and a program that allows an information processor to execute this control method.

(Basic Configuration)

Figure 1:
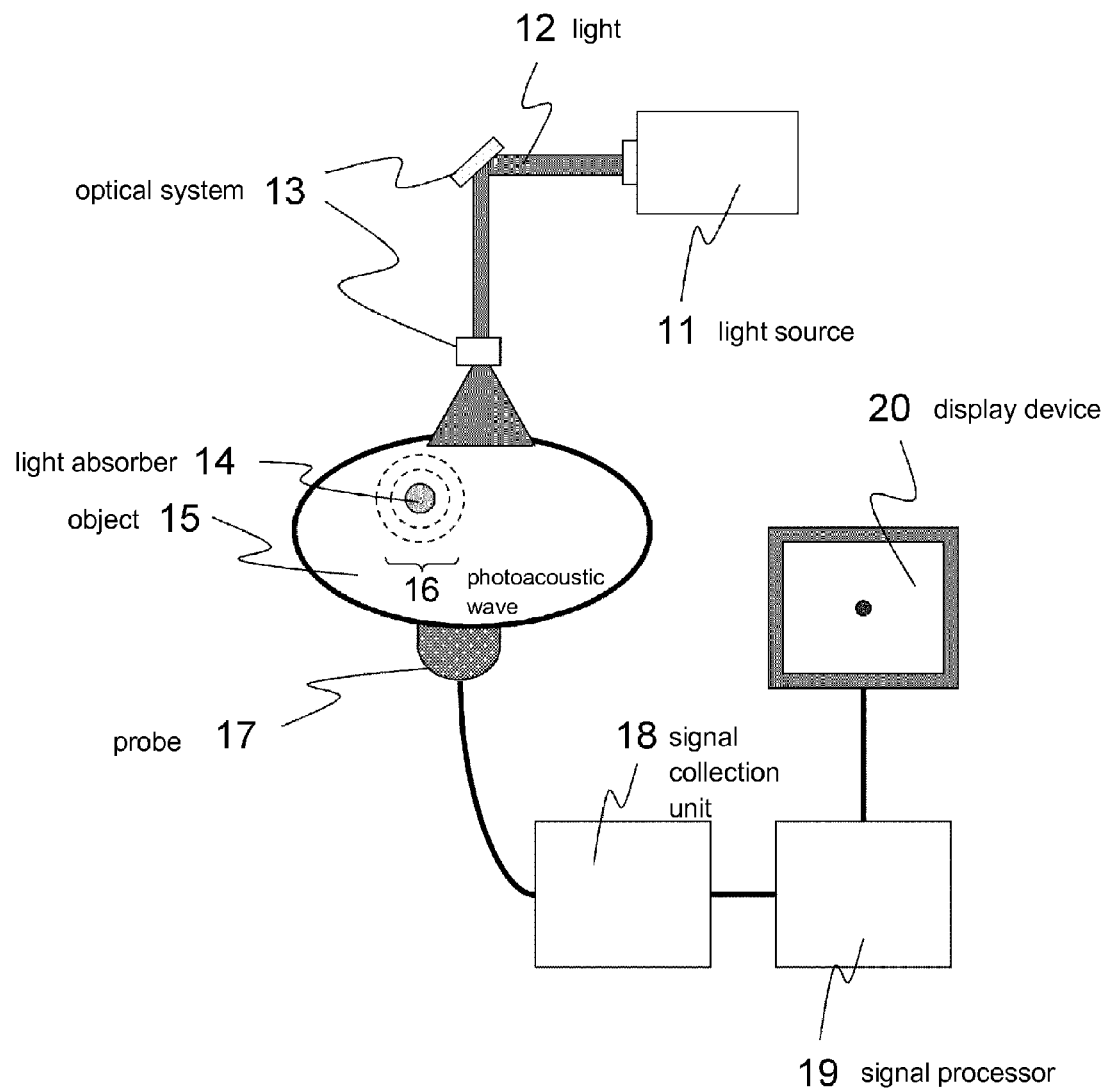
FIG. 1 is a schematic diagram depicting an example of a photoacoustic imaging apparatus.

FIG. 1 is a configuration diagram depicting an example of a photoacoustic imaging apparatus. Hereafter as a rule the same composing elements are denoted with a same reference number, and redundant description is omitted.

As a basic hardware configuration, the photoacoustic imaging apparatus has a light source 11, a probe 17 to detect a photoacoustic wave, and a signal processor 19. Light 12 irradiated from the light source 11 is processed by an optical system 13 and irradiated onto an object 15. If a part of the energy of light propagated inside the object 15 is absorbed by a light absorber 14, such as a blood vessel, a photoacoustic wave 16 is generated due to the thermal expansion of the light absorber 14. The photoacoustic wave 16 is detected by the probe 17 and is converted into an analog signal. The analog signal is amplified and converted into a digital signal by a signal collection unit 18. The digital signal is converted into characteristic information or digital data on an area inside the object by the signal processor 19 and is displayed on a display device 20.

(Photoacoustic Imaging Method)

Now processing performed by the signal processor 19 will be described with reference to FIG. 2 and FIG. 3. Particularly in image reconstruction under a limited view condition, processing to decrease artifacts due to the limited view and to accurately reproduce the shape of a light absorber, in other words, a photoacoustic wave generation source (sound source) will be described.

First an overview of processing by the signal processor 19 will be described with reference to FIG. 2.

Processing 1 (Step S201): Step of Generating a Data Group to Represent a Signal to be Received by Each Detection Element from a Photoacoustic Wave Generated from a Micro Sound Source in a Target Area Inside an Object Among image reconstruction methods, there is a method called a "model based method" and an "iterative reconstruction method". In the model based method, the propagation of an acoustic wave generated inside an object is modeled, and a photoacoustic signal to be acquired is estimated by performing simulation based on the model. Then optical characteristic value distribution (particularly initial sound pressure distribution) inside the object is estimated, so that the difference between the estimated value and an actually measured value by the probe is minimized. In the model based method, a mathematical expression to analytically solve a photoacoustic wave equation under a certain assumption is used as a propagation model in many cases. For example, the following Expression (1) is a propagation model when it is assumed that the sound velocity in an object is steady.

[Math. 1]

$$p(r_d, t) = \frac{1}{4\pi c^2} \frac{\partial}{\partial t}\left[\frac{1}{ct}\int dr \cdot p_0(r)\delta\left(t - \frac{|r-r_d|}{c}\right)\right] \quad (1)$$

where $p(r_d, t)$ is an ideal photoacoustic signal detected at time t at a position $r_d$ of the probe, c is a sound velocity, $p_0(r)$ is an initial sound pressure distribution, and $\delta$ is a delta function.

If the space is discretized and expressed as a matrix for a linear problem in Expression (1), then Expression (1) is given by the following Expression (2).

$$p_d = A \cdot p_0 \quad (2)$$

Here $p_d$ is a column vector that expresses a photoacoustic wave signal detected by the probe, and $p_0$ is a column vector that expresses a discretized initial sound pressure distribution. A is a forward model matrix (an operator expressed by a matrix) to express that a photoacoustic wave generated from a micro sound source is detected by the probe, and converted into a photoacoustic signal. Normally to accurately model the propagation and reception characteristics of the photoacoustic wave, the forward model matrix A is generated considering the reception characteristic of the probe (e.g. element size effect, impulse response), pulse width of the incident light, reflection and attenuation of the photoacoustic wave or the like. In the present invention as well, it is preferable to generate a forward model matrix conforming to a physical model of a system to be measured.

By this processing, a data group used for the image reconstruction is generated from the photoacoustic wave that is originated from the micro sound source in the target area inside the object.

Processing 2 (Step 202): Step of Calculating a Solution Including Many Characteristic Structures of the Measurement Target Inside the Object as an Optimum Solution A detection signal group, which is obtained by receiving a photoacoustic wave generated from the object by each detection element of the probe 17, is assumed to be a column vector ($p_d$). The forward model matrix determined in Processing 1 is assumed to be A. Then the column vector $p_0$ of the initial sound pressure distribution, which is the optical characteristic value distribution inside the object, is given by Expression (2). If the matrix A is regular at this time, the initial sound pressure distribution $p_0$ is given by the following Expression (3), since the matrix A has an inverse matrix $A^{-1}$.

$$p_0 = A^{-1} \cdot p_d \quad (3)$$

As shown in Expression (3), the initial sound pressure distribution $p_0$ is determined by multiplying the detected sound pressure vector by the inverse matrix of the matrix A. If noise $\epsilon$ is superimposed on the detection signal group $p_d$, a pseudo inverse matrix $(A^T A)^{-1} A^T$ is used instead of the inverse matrix $A^{-1}$, for the optimum solution $(\hat{p}_0)$ of the initial sound pressure distribution. Here superscript T indicates the transposition of the matrix.

Under the limited view condition, which is a prerequisite of the present invention, the matrix A is not regular and therefore has no inverse matrix. Furthermore, if the pseudo inverse matrix is insufficient, then a conditional optimization problem must be solved to determine the $p_0$ in order to minimize a cost function in Expression (4).

[Math. 2]

$$\hat{p}_0 = \underset{p_0}{\operatorname{argmin}} \|p_d - A \cdot p_0\|^2 + \lambda \cdot f(p_0) \quad (4)$$

In Expression (4), the first term on the right side is a least square cost function, and $f(p_0)$ of the second term is a constraint term or a penalty term. The second term assigns a constraint to the solution of the least square cost function of the first term, so as to make the solution more appropriate (regularization term). $\lambda$ is an arbitrary constant and is determined empirically to balance the least square term and the constraint term.

For a general constraint term, a norm of the initial sound pressure distribution $p_0$ (two norms), that is Expression (5), is used. A constraint shown in Expression (6), to minimize the total variation, that is, another index to indicate the smoothness of an image, is also used often.

[Math. 3]

$$f(p_0) = \|p_0\|_2^2 \quad (5)$$

$$f(p_0) = \|\nabla p_0\|_1 \quad (6)$$

However after the result of an examination, the present inventors discovered that the shape of a photoacoustic wave generation source cannot be accurately reproduced under a limited view condition if such general constraints are used. Then after further examination, the present inventors discovered that constraints specific to an image of photoacoustic imaging are required to reproduce the shape of the photoacoustic wave generation source.

For example, if a living organism is imaged using light in a visible region and near infrared region (wavelength: 500 to 900 nm), blood vessels (blood) containing lots of hemoglobin are imaged, since the absorption coefficient of hemoglobin is higher than other tissue (e.g. lipids, water) in these wavelength regions. In this case, an estimated solution $(\hat{p}_0)$ is expected to include many structural characteristics of the blood vessel. Thus the characteristic structure differs depending on the wavelength of the light and the segment to be measured, and constraints also change accordingly. Therefore a photoacoustic wave originating from a micro sound source to be measured has a characteristic reflecting the shape of an object to be imaged.

For example, Murray's Law is known as a branch model of blood vessels representing the structural characteristics of the blood vessels. As FIG. 3 shows, according to Murray's Law, the relationship of the thickness of a blood vessel before branching ($r_0$) and the thickness of the blood vessel after branching ($r_1$ and $r_2$) is given by Expression (7).

$$r_0^3 = r_1^3 + r_2^3 \quad (7)$$

Branching angles after branching ($\theta_1$ and $\theta^2$) are given by Expression (8) and Expression (9).

[Math. 4]

$$\cos\theta_1 = \frac{r_0^4 + r_1^4 - r_2^4}{2 r_0^2 r_1^2} \quad (8)$$

$$\cos\theta_2 = \frac{r_0^4 + r_2^4 - r_1^4}{2 r_0^2 r_2^2} \quad (9)$$

Since the image of blood vessels has these characteristics, the condition of the following Expression (1) must be minimized to estimate an image including many such characteristics.

[Math. 5]

$$f(p_0) = p_0 \left( \|r_0^3 - r_1^3 - r_2^3\|_2^2 + \left\|\cos\theta_1 - \frac{r_0^4 + r_1^4 - r_2^4}{2 r_0^2 r_1^2}\right\|_2^2 + \left\|\cos\theta_2 - \frac{r_0^4 + r_2^4 - r_1^4}{2 r_0^2 r_2^2}\right\|_2^2 \right) \quad (10)$$

In other words, the initial sound pressure distribution can be reproduced even under a limited view condition by solving Expression (4) using Expression (10), which is a constraint term including many structures to satisfy the conditions of Expression (7) to Expression (9) out of the least square solutions of $p_0$. If the measurement target segment is a blood vessel, this method of applying Murray's Law is used.

Furthermore, if a pattern of a structure of the measurement target blood vessel is somewhat known in the result of a basic examination using a photoacoustic microscope, for example, it is assumed that the image of the blood vessel can be developed using a base $\phi$. FIG. 4A and FIG. 4B are examples of a pattern of a blood vessel structure. Two patterns are shown here, but other patterns are also possible.

[Math. 6]

$$p_{0,vessel} = a_0 \phi_0 + a_1 \phi_1 + a_2 \phi_2 + \ldots + a_n \phi_n = \Sigma_{i=0}^n a_i \phi i \quad (11)$$

Then the bases ($\phi_0$ - - - $\phi_n$), which represent the characteristic structure, are calculated from a plurality of photoacoustic images of blood vessels. If a solution including many bases $\phi$ is estimated, the shape of the sound source can be reproduced even under a limited view condition. In concrete terms, if the base matrix is expressed as $\phi(\phi_0$ - - - $\phi_n)$, then the cost function of the following Expression (12) is minimized.

[Math. 7]

$$\hat{p}_0 = \underset{p_0}{\operatorname{argmin}} \|A p_0 - p_d\|^2 + \lambda \|\Phi p_0\|_1 \quad (12)$$

Here an example of imaging blood vessels in photoacoustic imaging was shown. However a structure of tissue other than blood vessels may be imaged depending on the wavelength of the light to be used and the measurement target segment. For example, plaque that contains a lot of lipids, or a tissue that contains a lot of melanin can be imaged. In other words, the essence of the present invention is to select a solution that includes many characteristic structures of the measurement target as an optimum solution, and the measurement target is not limited to blood vessels.

By performing the above steps, even if an acoustic wave can be received only from a specific direction, not from all around the closed surface surrounding the object (under a limited view condition), artifacts due to insufficient reception information can be decreased and the shape of the photoacoustic wave generation source can be accurately reproduced. In other words, artifacts can be decreased, and the reproducibility of the shape of the sound wave generation source can be increased even under a limited view condition.

Now the major composing elements of the apparatus will be described.

(Light Source 11)

The light source 11 irradiates light onto an object. If the object is an organism, the light source 11 irradiates light of a wavelength that is absorbed by a specific component inside the object. The light source may be integrated with the photoacoustic imaging apparatus or may be a standalone unit.

For the light source, a pulsed light source that can generate pulsed light at a several nanosecond to several hundred nanosecond order is preferred. A pulsed width of about 10 nanoseconds is particularly preferable to efficiently generate photoacoustic waves. For the light source, laser is preferable since high power can be obtained. A light emitting diode or the like may be used instead. For the laser, various lasers including a solid-state laser, a gas laser, a fiber laser, a dye laser and a semiconductor laser can be used. Irradiation timing, wave form, intensity or the like are controlled by a light source control unit (not illustrated).

In this invention, if the object is an organism, it is preferable to use the wavelength of light which allows the light to propagate inside the object. In concrete terms, such a wavelength is 500 nm or more, 1200 nm or less.

(Optical System 13)

The light 12 irradiated from the light source 11 is guided to the object while being processed to be a desired light distribution shape by the optical system 13, which includes a lens, a mirror, an optical fiber and a diffusion plate. The optical system 13 to be used can be any optical system only if the light 12 emitted from the light source is irradiated to have a desired shape. It is preferable that the light is spread to be a certain size of area rather than being condensed by a lens, in terms of safety of an object and broadening of a diagnosis area.

(Object 15 and Light Absorber 14)

The object 15 and the light absorber 14 are not composing elements of the photoacoustic imaging apparatus of the present invention, but will be described hereinbelow. A main purpose of the photoacoustic imaging apparatus of the present invention is the diagnosis of a malignant tumor and vascular diseases of a human and animal, and follow up observation of chemotherapy. Therefore an assumed object 15 is a segment of an organism to be diagnosed, such as a breast, fingers and limbs of a human and animal. As a light absorber 14 in the object, a segment of which absorption coefficient is relatively high inside the object is assumed. For example, if the measurement target is a human body, the light absorber 14 could be oxyhemoglobin, deoxyhemoglobin, blood vessels containing a lot of hemoglobin, or a malignant tumor that includes many new blood vessels. A light absorber on the surface of an object is, for example, melanin existing near the surface of the skin.

(Probe 17)

The probe 17 detects an acoustic wave (in particular, an photoacoustic wave from the object), and converts the acoustic wave into an analog electric signal. For the probe 17, a transducer using piezoelectric phenomena, a transducer using optical resonance, a transducer using a change in capacitance or the like can be used. In the probe 17, it is preferable that a plurality of detection elements are one dimensionally or two dimensionally arrayed. By using such multi-dimensional array elements, an acoustic wave can be detected simultaneously at a plurality of locations, hence a shortening of detection time and a decrease in the influence of vibration of the object can be expected. The probe, constituted by the detection elements that are one dimensionally or two dimensionally arrayed on a plane, cannot measure from all around the closed surface surrounding the object, but can contact the object only from a predetermined direction. Therefore the problem of a limited view condition is generated.

(Signal Collection Unit 18)

The signal collection unit 18 amplifies an analog electric signal acquired by the probe 17 and converts this signal into a digital signal. The signal collection unit 18 is typically constituted by an amplifier, an A/D convertor, a field programmable gate array (FPGA) chip or the like. If a plurality of detection signals is acquired by the probe, it is preferable that the plurality of signals can be processed simultaneously. Thereby the time to form an image can be decreased. In this description, "detection signal" is a concept that includes both an analog signal acquired by the probe 17 and a digital signal generated by performing A/D conversion on this analog signal. The detection signal is also called a "photoacoustic signal".

(Signal Processor 19)

The signal processor 19 acquires image data of an area inside the object by image reconstruction. In many cases a workstation is used for the signal processor 19, and image reconstruction processing or the like is performed according to preprogrammed software. An example of the software module configuration is a two-module configuration constituted by a signal processing module that performs noise reduction processing for a detection signal, and an image reconstruction module that performs image reconstruction using a signal processed by the signal processing module. In the image reconstruction module, image data is created by the image construction shown in Processing 2 (step S202).

It is preferable that the signal processor 19 includes a memory that stores a forward model matrix A generated in Processing 1 (step S201), which is a characteristic of the present invention. Normally the size of this matrix A is large, hence performing data compression is preferable. The compression method can be, for example, a method of storing only values other than zero, or a method assuming that signals exceeding a certain reception angle are not received, considering the directivity of the probe. In order to decrease the operation volume by the signal processor 19, only a pseudo inverse matrix of the matrix A or data after performing singular value decomposition on the matrix A may be stored. In other words, it is not absolutely necessary to store the matrix A itself.

The signal collection unit 18 and the signal processor 19 may be integrated. In this case, the image data of the object may be generated not by software processing performed by a workstation but by hardware processing.

(Display Device 20)

The display device 20 displays image data that is outputted from the signal processor 19. Typically a liquid crystal display or the like is used. The display device 20 may be disposed separately from the photoacoustic imaging apparatus.

Example 1

An example of the photoacoustic imaging, to which the present invention is applied, will be described. If necessary, the configuration diagram in FIG. 1 and the flow chart in FIG. 2 are referred to in the description.

In this example, a Ti: sa laser system excited by a double wave YAG laser is used as the light source 11. In this laser system, light of a 700 nm to 900 nm wavelength can be irradiated. The laser beam is expanded to about 1 cm radius using the optical system 13, including a mirror and a beam expander, and is then set so as to be irradiated onto an object. The probe 17 used here is a two-dimensional array type piezoelectric probe having 18×18 elements. The signal collection unit 18 has a function to simultaneously receive 324 channel-analog signals from the probe, amplify the signals and convert the signals into digital signals. Here a PC is used as the signal processor 19. The object 15 is a phantom simulating an organism created by 1% intra-lipids and diluted ink solidified by agar. As the light absorber 14, a wire covered with black rubber, of which diameter is 0.5 mm, is embedded in this phantom. The wire as the light absorber is branched in a T shape to simulate a blood vessel.

Figure 2:
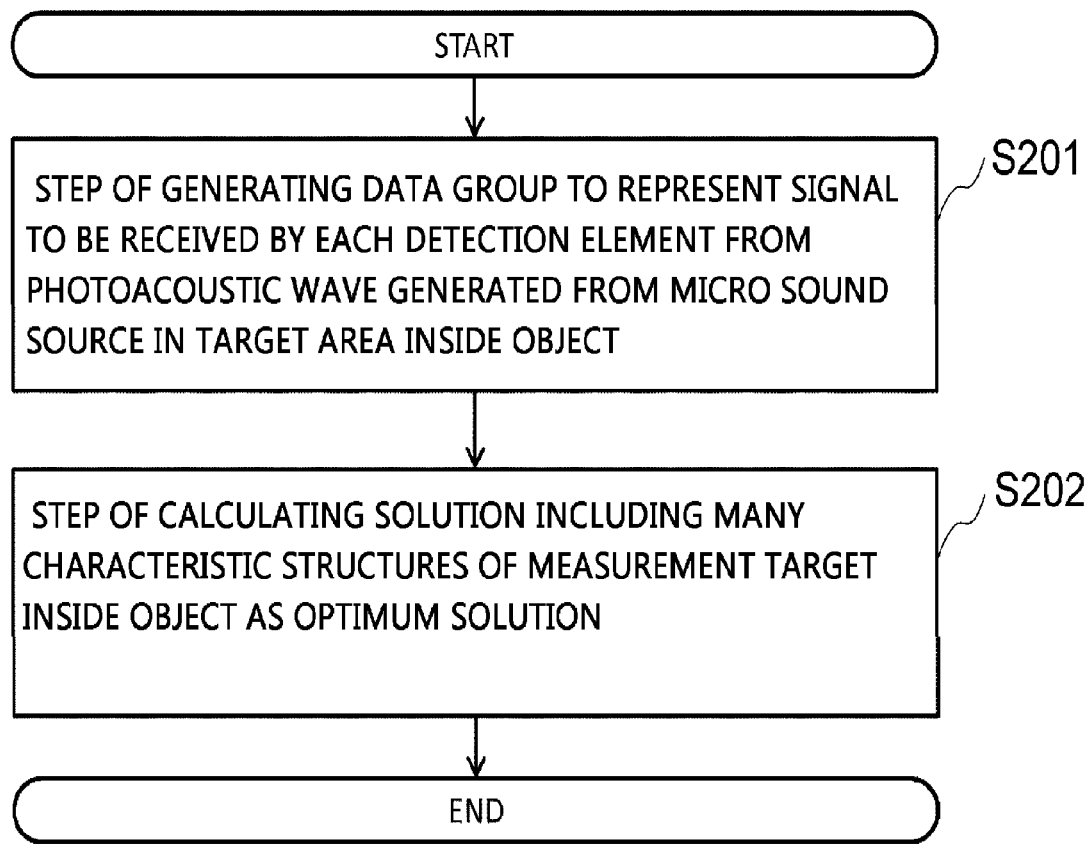
FIG. 2 is a flow chart depicting an example of detection signal processing.
Figure 3:
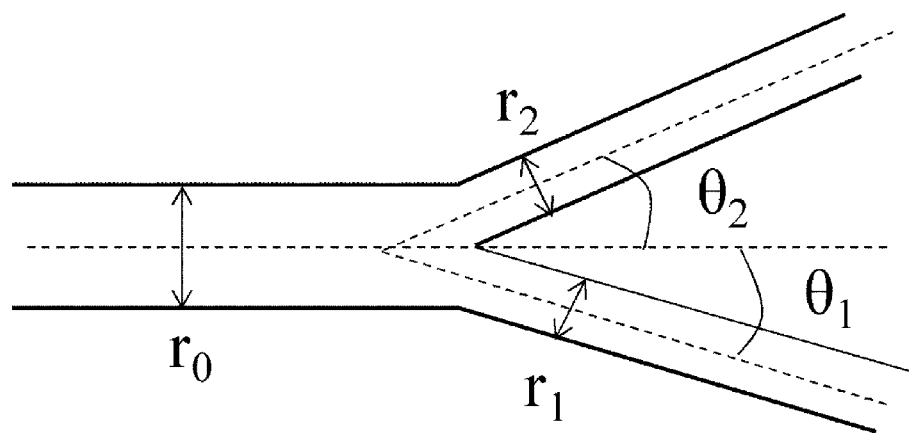
FIG. 3 is a diagram depicting an example of a branch model of a blood vessel.

First as shown in Processing 1 (step S201) in FIG. 2, a forward model matrix A, which is modeling an acoustic wave propagation in the phantom, is calculated. This matrix A, which is large sized but is a sparse matrix, is compressed using a method of holding values other than zero, and is then stored in memory of the PC that functions as the signal processor.

Then the phantom is set in the apparatus, and light of a 800 nm wavelength is irradiated. Since the probe is set so as to contact one surface of the phantom, the measurement is performed under the limited view condition, where only a photoacoustic wave in a specific direction is measured.

The detection signal $p_d$, acquired under this condition, is stored in the memory of the PC after noise is reduced by the signal processing module of the PC. Then in the image reconstruction module, the image reconstruction processing shown in Processing 2 (step S202) in FIG. 2 is performed, and the optical characteristic value distribution (initial sound pressure distribution) is calculated. Here Expression (4) is solved with a constraint where a wire-like light absorber in the phantom branches according to Murray's Law. In concrete terms, iterative calculation is performed using the following Expression (13).

$$p_0^{k+1} = p_0^k + \gamma A(p_d - A p_0^k) \quad (13)$$

Figure 5A:
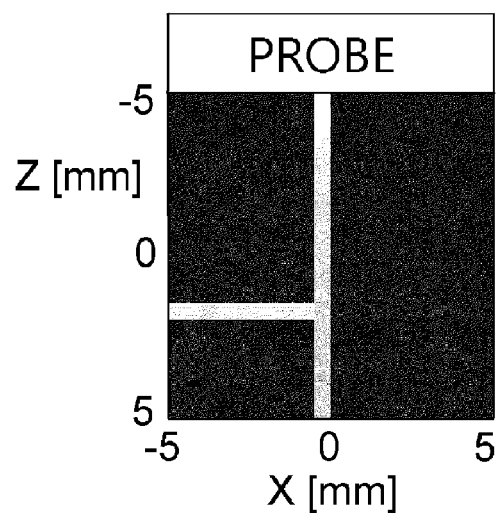
FIG. 5A and FIG. 5B are diagrams depicting initial sound pressure distribution according to the present invention, and a prior art.
Figure 5B:
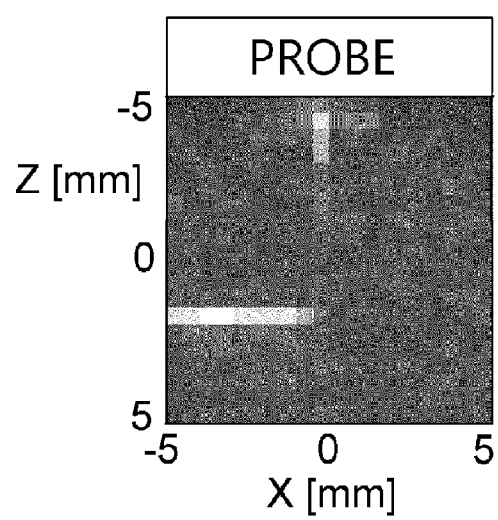

In this example, a certain threshold is set and each $p_0$ determined by the iterative calculation is binarized into values higher than the threshold and values lower than the threshold. A voxel area where the values are higher is assumed to conform to Murray's Law, and a voxel area where the values are lower (does not conform to Murray's Law) are set to a zero value. By repeating this constraint, $p_0$, of which residual error is a predetermined set value or less, is regarded as an optimum solution. FIG. 5A is an example of the reconstructed image acquired in this case. For comparison, FIG. 5B shows a result of the image generated by reconstructing the acquired $p_d$ according to the back projection method (a conventional method). In both images, the probe is disposed in an area where the Z axis value is negative.

FIG. 5A and FIG. 5B are compared. In FIG. 5A, where the present invention is applied, the light absorber, which is a T-shaped wire disposed inside the phantom, is almost perfectly reproduced. However in FIG. 5B where the conventional back projection method is applied, the shape of the wire of the light absorber, located in parallel with the detection surface of the probe, is reproduced, but the wire of the light absorber, located perpendicular to the detection surface, is hardly reproduced. Further in FIG. 5B, many artifacts exist and the shape of the light absorber or the like is not clear.

Thus if a characteristic structure of the measurement target object is used for the constraint in the image reconstruction, the generation source of the photoacoustic wave can be reproduced almost perfectly, even if the photoacoustic wave is measured under the limited view condition.

Example 2

An example of the photoacoustic imaging, to which a reconstruction method which is different from Example 1 is applied, will be described as Example 2. The basic configuration of the apparatus according to Example 2 is the same as that of Example 1. The object 15 is also a phantom simulating an organism, in the same manner as Example 1. Since the probe contacts one surface of the phantom, the measurement is performed under the limited view condition, in the same manner as Example 1.

First as shown in Processing 1 (step S201) in FIG. 2, a forward model matrix A, which considers the acoustic wave propagation in the phantom and the characteristics of the probe, is calculated. Then the phantom is set in the apparatus and the light of a 800 nm wavelength is irradiated. The noise reduction processing is performed on a detection signal $p_d$ acquired at this time, in the same manner as Example 1. Then in the image reconstruction module, the image reconstruction processing shown in Processing 2 (step S202) in FIG. 2 is performed, and the initial sound pressure distribution is calculated. Here a base is calculated from a plurality of blood vessel images shown in FIG. 4, and a solution that includes the many bases mentioned above is selected.

In the reconstruction, various three-dimensional blood vessels are imaged first using a photoacoustic microscope or the like. Then only images having blood vessel shapes are extracted by performing such image processing as filtering processing on the blood vessel images, so as to create three-dimensional blood vessel data. Then handling the plurality of three-dimensional blood vessel data (binarized voxel data) as a one-dimensional vector, a three-dimensional eigen image (one-dimensional eigen vector) is calculated by eigen value developing. Further a base matrix φ, where the three-dimensional eigen images are arranged in the column direction, is generated, and Expression (11) is solved using the base matrix φ. Here the eigen image is a characteristic structure of the blood vessel, and a blood vessel is expressed by a combination of eigen images. In other words, the initial sound pressure distribution $p_0$ that includes many characteristic structures (bases) is calculated as an optimum solution by solving an optimization problem for minimizing a coefficient generated by developing the initial sound pressure distribution $p_0$ with the base matrix φ constituted by the eigen vectors.

The reconstructed image acquired as a result reproduces the light absorber embedded in the phantom almost perfectly, as shown in FIG. 5A. If the image is reconstructed according to the model based method which assumes that the image is smooth, on the other hand, the light absorber in the phantom cannot be perfectly reproduced, as shown in FIG. 5B.

Thus if a characteristic structure of the measurement target object is used for the constraint in the image reconstruction, the generation source of the photoacoustic wave can be reproduced almost perfectly, even if the photoacoustic wave is measured under the limited view condition.

Example 3

An example of the photoacoustic imaging apparatus, in which the measurement target object is plaque, will be described as Example 3. The basic configuration of the apparatus according to Embodiment 3 is the same as that of Embodiment 1. In Embodiment 3, an OPO laser is used as the light source. A phantom simulating an organism is used for the object 15. Unlike Example 1, the light absorber embedded in the phantom simulates spherical lipids. In the same manner as Example 1, the probe contacts one surface of the phantom, and the measurement is performed under the limited view condition.

First as shown in Processing 1 (step S201) in FIG. 2, a forward model matrix A, which considers the acoustic wave propagation in the phantom and the characteristics of the probe, is calculated. Then the phantom is set in the apparatus, and the light of a 1210 nm wavelength is irradiated. The noise reduction processing is performed on a detection signal $p_d$ acquired at this time, in the same manner as Example 1. Then in the image reconstruction module, the image reconstruction processing shown in Processing 2 (step S202) in FIG. 2 is performed, and the initial sound distribution is calculated. Here the image is reconstructed by using an iterative calculation in the same manner as Example 1, adding a constraint that the measurement target object is a sphere.

As a result, the spherical light absorber, which is the measurement target object, is almost perfectly reproduced. However in the case of the back projection method using the same measurement data, the shape of the sphere can be reproduced, but streak artifacts are generated and the image deteriorates.

Thus if the characteristic structure of the measurement target object is used for the constraint in the image reconstruction, the generation source of the photoacoustic wave, other than blood vessels, can also be reproduced almost perfectly, even if the photoacoustic wave is measured under the limited view condition.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., non-transitory computer-readable medium). Therefore, the computer (including the device such as a CPU or MPU), the method, the program (including a program code and a program product), and the non-transitory computer-readable medium recording the program are all included within the scope of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-057791, filed on Mar. 21, 2013, which is hereby incorporated by reference herein its entirety.

What is claimed is:

1. An object information acquiring apparatus, comprising:
a light source configured to irradiate light into an object;
a probe configured to detect an acoustic wave generated from said object onto which said light is irradiated and convert said detected acoustic wave into a detection signal; and
a signal processor configured to obtain characteristic information inside the object based on the detection signal, according to a model-based method for selecting an optimum solution from a plurality of solutions,
wherein the signal processor is configured to reconstruct, as the optimum solution, the characteristic information according to the model-based method using a regularization term, for constraint to selection of the optimum solution from the plurality of solutions, based on information regarding a characteristic structure of a measurement target inside the object, wherein the measurement target is blood vessels.

2. The object information acquiring apparatus according to claim 1, wherein the probe is formed of a plurality of detection elements that are arranged one dimensionally or two dimensionally.

3. The object information acquiring apparatus according to claim 1, wherein the probe detects said acoustic wave from a specific direction.

4. The object information acquiring apparatus according to claim 1, wherein the signal processor reconstructs the characteristic information by solving an optimization problem of which constraint is a cost function with the regularization term.

5. The object information acquiring apparatus according to claim 1, wherein the signal processor is configured to use the regularization term based on the characteristic structure of the blood vessels from a plurality of blood vessel images.

6. The object information acquiring apparatus according to claim 5, wherein the signal processor is configured to use the regularization term based on the characteristic structure of the blood vessels by obtaining bases from the plurality of blood vessel images.

7. The object information acquiring apparatus according to claim 5, wherein the signal processor is configured to use the regularization term based on the characteristic structure of the blood vessels on the basis of a physical model of the blood vessels.

8. The object information acquiring apparatus according to claim 7, wherein the signal processor is configured to use the regularization term such that when more characteristic structures are included in the characteristic information the cost function becomes smaller.

9. The object information acquiring apparatus according to claim 8, wherein the signal processor is configured to use the regularization term such that when more bases corresponding to the characteristic structure are included in the characteristic information the cost function becomes smaller.

10. The object information acquiring apparatus according to claim 1, wherein the measurement target inside the object is blood vessels, and the signal processor is configured to use the regularization term so as to include a term $r_0^3 - r_1^3 - r_2^3$, in which $r_0$ is a thickness of the blood vessel before branching, and $r_1$ and $r_2$ are thicknesses of the blood vessels after branching.

11. The object information acquiring apparatus according to claim 1, wherein the measurement target inside the object is blood vessels, and the signal processor is configured to use the regularization term so as to include terms $$\cos\theta_1 = \frac{r_0^4 + r_1^4 - r_2^4}{2r_0^2 r_1^2} \text{ and } \cos\theta_2 = \frac{r_0^4 + r_2^4 - r_1^4}{2r_0^2 r_2^2},$$

in which $r_0$ is a thickness of the blood vessel before branching, $r_1$ and $r_2$ are thicknesses of the blood vessels after branching, and $\theta_1$ and $\theta_2$ are branching angles for the blood vessels after branching.

12. The object information acquiring apparatus according to claim 1, wherein the measurement target inside the object is blood vessels, and the signal processor is configured to use the regularization term so as to include terms $r_0^3 - r_1^3 - r_2^3$, $$\cos\theta_1 = \frac{r_0^4 + r_1^4 - r_2^4}{2r_0^2 r_1^2} \text{ and } \cos\theta_2 = \frac{r_0^4 + r_2^4 - r_1^4}{2r_0^2 r_2^2},$$

in which $r_0$ is a thickness of the blood vessel before branching, $r_1$ and $r_2$ are thicknesses of the blood vessels after branching, and $\theta_1$ and $\theta_2$ are branching angles for the blood vessels after branching.

13. The object information acquiring apparatus according to claim 1, wherein the signal processing unit is configured to reconstruct the characteristic information according to the model-based method by performing a process including steps of:

calculating an estimated detection signal using a propagation model, the estimated detection signal being a signal that the probe is assumed to detect when receiving an acoustic wave from a sound source, and obtaining, as the characteristic information, an initial sound pressure distribution which minimizes a cost function including the regularization term and a term representing a difference between the detection signal and the estimated detection signal.

14. The object information acquiring apparatus according to claim 1, wherein the signal processor is configured to reconstruct the characteristic information according to the model-based method using the regularization term, for constraint to selection of the optimum solution which includes the characteristic structure of the measurement target.

15. A signal processing method, comprising:

obtaining a detection signal which is outputted from a probe by converting an acoustic wave generated from an object onto which light is irradiated; and obtaining characteristic information inside the object based on the detection signal, according to a model-based method for selecting an optimum solution from a plurality of solutions, wherein the characteristic information is reconstructed, as the optimum solution, according to a model based method using a regularization term, for constraint to selection of the optimum solution from the plurality of solutions, based on information regarding a characteristic structure of a measurement target inside the object, wherein the measurement target is blood vessels.

* * * * *